United States Patent
Leung et al.

(10) Patent No.: US 8,507,717 B2
(45) Date of Patent: *Aug. 13, 2013

(54) PRODUCTION OF SUBSTITUTED PHENYLENE AROMATIC DIESTERS

(75) Inventors: Tak W. Leung, Houston, TX (US); Gary A. Roth, Midland, MI (US); Tao Tao, Houston, TX (US); Kuanqiang Gao, Pearland, TX (US); Linfeng Chen, Missouri City, TX (US)

(73) Assignee: Dow Global Technologies LLC, Midland, MI (US)

( * ) Notice: Subject to any disclaimer, the term of this patent is extended or adjusted under 35 U.S.C. 154(b) by 605 days.

This patent is subject to a terminal disclaimer.

(21) Appl. No.: 12/651,142

(22) Filed: Dec. 31, 2009

(65) Prior Publication Data
US 2010/0174105 A1    Jul. 8, 2010

Related U.S. Application Data

(60) Provisional application No. 61/141,902, filed on Dec. 31, 2008, provisional application No. 61/141,959, filed on Dec. 31, 2008.

(51) Int. Cl.
*C07C 69/76* (2006.01)

(52) U.S. Cl.
USPC .......................................................... 560/85

(58) Field of Classification Search
None
See application file for complete search history.

(56) References Cited

U.S. PATENT DOCUMENTS
4,614,830 A * 9/1986 Philion ..................... 560/109

OTHER PUBLICATIONS

Schneider et al. (European Journal of Organic Chemistry, 2001, (16), 3055).*
Muller, et al., Stabile Semichinonsalze, Liebigs Ann. Chem., vol. 688, 1965, p. 134-149.
Muller et al., Zur Kenntnis neuer Brenzcatechine und orthe-chinone, Z. Naturforschg., vol. 18b, 1963, p. 1002-1009.

* cited by examiner

*Primary Examiner* — Susanna Moore
*Assistant Examiner* — Jennifer C Sawyer
(74) *Attorney, Agent, or Firm* — Whyte Hirschboeck Dudek S.C.

(57) ABSTRACT

The present disclosure is directed to the production of 5-tert-butyl-3-methyl-1,2-phenylene dibenzoate and the purification thereof. Synthesis pathways for a precursor to 5-tert-butyl-3-methyl-1,2-phenylene dibenzoate are provided. The precursor is 5-tert-butyl-3-methylcatechol.

19 Claims, 2 Drawing Sheets

Fig. 1

BMPD formation

Fig. 2

PRODUCTION OF SUBSTITUTED PHENYLENE AROMATIC DIESTERS

PRIORITY CLAIM

The present application claims priority to U.S. provisional application No. 61/141,902 filed on Dec. 31, 2008 and U.S. provisional application No. 61/141,959 filed on Dec. 31, 2008, the entire content of each application incorporated by reference herein.

BACKGROUND

The present disclosure relates to the production of substituted phenylene aromatic diesters.

Substituted phenylene aromatic diesters are used as internal electron donors in the preparation of procatalyst compositions for the production of olefin-based polymers. In particular, Ziegler-Natta catalysts containing 5-tert-butyl-3-methyl-1,2-phenylene dibenzoate as internal electron donor show high catalyst activity and high selectivity during polymerization. In addition, such catalysts produce olefin-based polymer (such as propylene-based polymer) with high isotacticity and broad molecular weight distribution.

The art recognizes the need for olefin-based polymers and propylene-based polymers with improved properties. Desired are multiple and/or alternate synthesis pathways for the production of substituted phenylene aromatic diester to ensure a cost-effective, and reliable supply of the same.

SUMMARY

The present disclosure is directed to the production of substituted phenylene aromatic diesters and 5-tert-butyl-3-methyl-1,2-phenylene dibenzoate in particular. Disclosed herein are synthesis pathways for the production of a precursor to the 5-tert-butyl-3-methyl-1,2-phenylene dibenzoate, namely 5-tert-butyl-3-methylcatechol. Provision of this precursor, as presented in this disclosure advantageously simplifies production of 5-tert-butyl-3-methyl-1,2-phenylene dibenzoate and enables large-scale production thereof with common, inexpensive starting materials.

The present disclosure provides a process. In an embodiment, a process is provided which includes reacting, under reaction conditions, 5-tert-butyl-3-methylcatechol (BMC) with an aromatic carboxylic acid or an aromatic carboxylic acid derivative, and forming 5-tert-butyl-3-methyl-1,2-phenylene dibenzoate (BMPD).

The disclosure provides another process. In an embodiment, a process is provided and includes alkylating, under reaction conditions, 3-methylcathecol with tert-butanol or isobutylene, and forming 5-tert-butyl-3-methylcatechol.

The disclosure provides another process. In an embodiment, a process is provided and includes oxidizing, under reaction conditions, 5-tert-butyl-3-methyl-2-hydroxybenzaldehyde, and forming 5-tert-butyl-3-methylcatechol.

The disclosure provides another process. In an embodiment, a process is provided and includes oxidizing, under reaction conditions, 4-tert-butyl-2-methylphenol, and forming 5-tert-butyl-3-methylcatechol.

The disclosure provides another process. In an embodiment, a process is provided and includes hydrolyzing, under reaction conditions, 2-halo-4-tert-butyl-6-methylphenol, and forming 5-tert-butyl-3-methylcatechol.

The disclosure provides another process. In an embodiment, a process is provided and includes hydrogenolyzing, under reaction conditions, 5-tert-butyl-3-aminomethylcatechol, and forming 5-tert-butyl-3-methylcatechol.

An advantage of the present disclosure is an improved process for the production of substituted phenylene aromatic diester, such as 5-tert-butyl-3-methyl-1,2-phenylene dibenzoate.

An advantage of the present disclosure is the provision of a precursor to 5-tert-butyl-3-methyl 1,2-phenylene dibenzoate, namely, 5-tert-butyl-3-methylcatechol.

An advantage of the present disclosure is the provision of a plurality of synthesis pathways to produce 5-tert-butyl-3-methylcatechol.

An advantage of the present disclosure is the production of 5-tert-butyl-3-methyl-1,2-phenylene dibenzoate using inexpensive starting materials.

An advantage of the present disclosure is numerous synthesis pathways for the production of substituted phenylene aromatic diester, such as 5-tert-butyl-3-methyl-1,2-phenylene dibenzoate, thereby ensuring a reliable supply of same for the production of propylene-based polymers.

An advantage of the present disclosure is a process for large scale production of substituted phenylene aromatic diester.

An advantage of the present disclosure is an environmentally-safe, non-toxic production process for substituted phenylene aromatic diester.

An advantage of the present disclosure is the large scale production of substituted phenylene aromatic diester.

An advantage of the present disclosure is a simple, time-effective, and/or cost-effective purification process for substituted phenylene aromatic diester.

DETAILED DESCRIPTION

The present disclosure is directed to the production of substituted phenylene aromatic diester. 5-tert-butyl-3-methylcatechol (or "BMC") is found to be an effective precursor for the production of the substituted phenylene aromatic diester, 5-tert-butyl-3-methyl-1,2-phenylene dibenzoate (or "BMPD"). BMPD is an effective internal electron donor in Ziegler-Natta catalysts. The processes disclosed herein advantageously provide economical (both time and monetary economies), simplified, up-scalable, synthesis pathways to BMC with yields acceptable for commercial/industrial application thereof. Economical access of BMC correspondingly contributes to economical production of 5-tert-butyl-3-methyl-1,2-phenylene dibenzoate.

5-tert-butyl-3-methylcatechol (BMC) has the structure (I) provided below.

(I)

In an embodiment, a process for producing BMC is provided. The process includes alkylating 3-methylcatechol with tert-butanol or isobutylene under reaction conditions, and forming 5-tert-butyl-3-methylcatechol (BMC) (Reaction 1 or Rx 1). The term "alkylating," or "alkylation," or "alkylation reaction" is the introduction of an alkyl radical into an organic compound. An "organic compound" is a chemical compound that contains a carbon atom. As used herein, "reaction conditions," are temperature, pressure, reactant concentrations, solvent concentrations, reactant mixing/addition parameters, and/or other conditions within a reaction vessel that promote reaction between the reagents and formation of the resultant product. In an embodiment, alkylation occurs with the addition of an inorganic acid (such as sulfuric acid) to a mixture of the 3-methylcatechol and the tert-butanol in heptane.

In an embodiment, the process includes the preparation of the 3-methylcatechol. The process includes oxidizing 2-hydroxy-3-methylbenzaldehyde under reaction conditions and forming the 3-methylcatechol (Rx 2). In a further embodiment, the oxidizing agent is a peroxide, such as hydrogen peroxide, which is added to the 2-hydroxy-3-methylaldehyde in an aqueous basic solution.

In an embodiment, the process includes the preparation of the 2-hydroxy-3-methylbenzaldehyde (Rx 3). The process includes formylating o-cresol with paraformaldehyde under reaction conditions, and forming 2-hydroxy-3-methylbenzaldehyde. The term "formylating," or "formylation," or "formylation reaction" is a chemical reaction whereby an organic compound is functionalized with a formyl group (—CH═O). The 2-hydroxy-3-methylbenzaldehyde is subsequently oxidized to form the 3-methylcatechol.

The formylation reaction may occur by formylating the o-cresol with paraformaldehyde, magnesium chloride ($MgCl_2$) and triethylamine ($Et_3N$) in refluxing tetrahydrofuran (THF). The reaction yields ortho-formylation of the o-cresol. Another suitable formylation reaction is the Reimer-Tiemann reaction (i.e., ortho-formylation of the o-cresol in chloroform/sodium hydroxide).

In an embodiment, 3-methylcatechol is prepared directly from o-cresol. The process includes oxidizing, under reaction conditions, o-cresol, and forming the 3-methylcatechol (Rx 4). In a further embodiment, the oxidizing agent is a peroxide, such as hydrogen peroxide. The process further includes alkylating the 3-methylcathecol and forming the BMC as disclosed above.

A nonlimiting representation of reactions 1, 2, and 3 is provided in pathway (II) below.

A nonlimiting representation of reaction 4 is provided in pathway (III) below.

In an embodiment, another process for producing BMC is provided. The process includes oxidizing 5-tert-butyl-3-methyl-2-hydroxybenzaldehyde, under reaction conditions, and forming 5-tert-butyl-3-methylcatechol (Rx 5). In a further embodiment, the oxidizing agent is a peroxide, such as hydrogen peroxide.

In an embodiment, the process includes synthesis of the 5-tert-butyl-3-methyl-2-hydroxybenzaldehyde. The process includes formylating, under reaction conditions, 4-tert-butyl-2-methylphenol with paraformaldehyde and forming the 5-tert-butyl-3-methyl-2-hydroxybenzaldehyde (Rx 6). Formylation may occur by way of any suitable formylation reaction as disclosed herein.

In an embodiment, the process includes the synthesis of the 4-tert-butyl-2-methylphenol. The process includes alkylating, under reaction conditions, o-cresol with isobutylene or t-butanol to form 4-tert-butyl-2-methylphenol (Rx 7). Alkylation may occur by way of any suitable alkylation reaction as disclosed herein. The compound, o-cresol, surprisingly has been found as an advantageous starting material for the production of BMC. The compound o-cresol is inexpensive and provides a methyl group directly adjacent to an —OH group on the aromatic ring. The —OH group of o-cresol is a strong para-director for an electrophilic substitution reaction, enabling ready alkylation of o-cresol to 4-tert-butyl-2-methylphenol. The 4-tert-butyl-2-methylphenol is subsequently formylated, under reaction conditions, to form the 5-tert-butyl-3-methyl-2-hydroxybenzaldehyde.

A nonlimiting representation of reactions 5, 6, and 7 is provided in pathway (IV) below.

A nonlimiting representation of reactions 8 and 9 is provided in pathway (V) below.

The present disclosure provides another process for producing BMC. In an embodiment, a process is provided and includes hydrolyzing, under reaction conditions, 2-halo-4-tert-butyl-6-methylphenol, and forming 5-tert-butyl-3-methylcatechol (Rx 10). As used herein, "hydrolyzing," or "hydrolysis," or "hydrolysis reaction" is a chemical reaction whereby water splits into H+ and OH− ions and the OH− ion replaces a functional group. The term "halo" is a halogen atom —F, Cl, Br, I. In an embodiment, the halogen atom is bromine yielding 2-bromo-4-tert-butyl-6-methylphenol. In another embodiment, the halogen atom is chlorine yielding 2-chloro-4-tert-butyl-6-methylphenol. In an embodiment, the hydrolysis reaction is catalyzed by a base and/or a salt, such as such as copper (II) sulfate.

In an embodiment, the process includes the synthesis of the 2-halo-4-tert-butyl-6-methylphenol. The process includes halogenating, under reaction conditions, 4-tert-butyl-2-methylphenol, and forming the 2-halo-4-tert-butyl-6-methylphenol (Rx 11). The term "halogenating," or "halogenation," or "halogenation reaction," is the introduction of a halogen radical into an organic compound. Halogenation occurs by reacting the 4-tert-butyl-2-methylphenol with a halogenating agent, such as a brominating agent or a chlorinating agent. Nonlimiting examples of suitable halogenating agents include N-bromosuccinamine (NBS), a brominating agent, and/or N-chlorosuccinamine (NCS), a chlorinating agent. Halogenation may also occur by reacting the 4-tert-butyl-2-methylphenol with elemental halogen. The term "$X_2$," in pathway (VI) below denotes the reaction with elemental halogen. The elemental halogen and may be $Cl_2$ or $Br_2$.

The present disclosure provides another process for producing BMC. In an embodiment, a process is provided and includes oxidizing, under reaction conditions, 4-tert-butyl-2-methylphenol, and forming 5-tert-butyl-3-methylcatechol (Rx 8). Oxidation may occur by way of addition of a peroxide to the 4-tert-butyl-2-methylcresol in a basic aqueous solution.

In an embodiment, the process includes synthesis of the 4-tert-butyl-2-methylphenol. The process includes alkylating, under reaction conditions, o-cresol with tert-butanol or isobutylene, and forming the 4-tert-butyl-2-methylphenol (Rx 9). Alkylation may occur by way of any suitable alkylation reaction as disclosed herein. The 4-tert-butyl-2-methylcresol is subsequently oxidized to form the BMC.

In an embodiment, the process includes synthesis of the 4-tert-butyl-2-methylphenol. The 4-tert-butyl-2-methylphenol is formed by alkylating, under reaction conditions, o-cresol with isobutylene or t-butanol as disclosed above (Rx 12). The 4-tert-butyl-2-methylphenol is subsequently halogenated to form the 2-halo-4-tert-butyl-6-methylphenol.

A nonlimiting representation of reactions 10, 11, and 12 is provided in pathway (VI) below.

A nonlimiting representation of reactions 13 and 14 is provided in pathway (VII) below.

The present disclosure provides another process for producing BMC. In an embodiment, a process is provided and includes hydrogenolyzing, under reaction conditions, 5-tert-butyl-3-aminomethylcatechol, and forming 5-tert-butyl-3-methylcatechol (Rx 13). The term "hydrogenolyzing," or "hydrogenolysis," or "hydrogenolysis reaction" is a chemical reaction whereby a carbon-carbon or carbon-heteroatom single bond is cleaved by hydrogen. Nonlimiting examples of suitable hydrogenolyzing agents include catalytic hydrogenolyzing agents (such as palladium catalysts) and borohydrides, such as sodium cyano-borohydride.

In an embodiment, the process includes the synthesis of the 5-tert-butyl-3-aminomethylcatechol. The process includes an aminoalkylating, under reaction conditions, 4-tert-butylcatechol, and forming the 5-tert-butyl-3-aminomethylcatechol (Rx 14). The 5-tert-butyl-3-aminomethylcatechol is subsequently hydrogenolyzed to form the 5-tert-butyl-3-methylcatechol. Aminoalkylation occurs by way of the Mannich reaction. The "Mannich reaction" is an organic reaction which aminoalkylates an acidic proton located next to a carbonyl functional group with formaldehyde and ammonia or any primary or secondary amine.

In an embodiment, a process for producing 5-tert-butyl-3-methyl-1,2-phenylene dibenzoate (BMPD) is provided. The process includes reacting BMC, under reaction conditions, with a member selected from an aromatic carboxylic acid and/or an aromatic carboxylic acid derivative, and subsequently forming 5-tert-butyl-3-methyl-1,2-phenylene dibenzoate (BMPD). The BMC is prepared by any of the synthesis pathways as previously disclosed herein.

As used herein, an "aromatic carboxylic acid" is a compound containing at least one benzene ring with at least one carboxyl group directly bonded to the benzene ring. It is understood that the aromatic carboxylic acid may be a monocyclic structure or a polycyclic structure. The aromatic carboxylic acid may be a mono- or a poly-carboxylic acid. Nonlimiting examples of suitable aromatic carboxylic acids include benzoic acid, 1-naphthoic acid, 2-naphthoic acid, 6H-phenalene-2-carboxylic acid, anthracene-2-carboxylic acid, phenanthrene-2-carboxylic acid, and phenanthrene-3-carboxylic acid.

A "derivative of an aromatic carboxylic acid" or "an aromatic carboxylic acid derivative," as used herein, is an aromatic acyl halide, an aromatic anhydride, an aromatic carboxylate salt, or any combination thereof. It is understood that the derivative of the aromatic carboxylic acid may be a monocyclic structure or a polycyclic structure. Nonlimiting examples of suitable aromatic acyl halides include halides of any of the aromatic carboxylic acids disclosed above (i.e., an acyl halide of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic acyl halides include benzoyl chloride, benzoyl fluoride, benzoyl bromide, and benzoyl iodide, naphthoyl chloride, naphthoyl fluoride, naphthoyl bromide, naphthoyl iodide, and any combination of the foregoing aromatic acyl halides.

Nonlimiting examples of suitable aromatic anhydrides include anhydride of the aromatic carboxylic acids disclosed above. (i.e., an anhydride of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic anhydrides include benzoic anhydride and any combination of the foregoing aromatic anhydrides.

Nonlimiting examples of suitable aromatic carboxylate salts include potassium, sodium, or lithium salt of the aromatic carboxylic acids disclosed above (i.e., salts of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic carboxylate salts include potassium benzoate, sodium benzoate, lithium benzoate, potassium 2-naphthoate, sodium 2-naphthoate, and any combination of the foregoing aromatic carboxylate salts.

The aromatic carboxylic acid, or derivative thereof may be substituted. The term "substituted aromatic carboxylic acid or derivative thereof," as used herein, is an aromatic carboxylic acid, or derivative thereof, whereby at least one of the benzene-ring substituents (other than the carboxyl group) is a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Thus, the term "substituted aromatic carboxylic acid or derivative thereof" includes substituted aromatic carboxylic acid, substituted aromatic acyl halide, substituted aromatic anhydride, and/or substituted aromatic carboxylate salt.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F, Cl, Br, I), N, O, P, B, S, and Si. A substituted hydrocarbyl group also includes a halohydrocarbyl group and/or a silicon-containing hydrocarbyl group. As used herein, the term "halohydrocarbyl group" refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

In an embodiment, BMPD is formed by reacting BMC, under reaction conditions, with an aromatic carboxylic acid derivative, benzoyl chloride. The process includes reacting BMC with benzoyl chloride in the presence of a base under reaction conditions, and forming BMPD (Rx 15). Nonlimiting examples of base include pyridine, triethylamine, trimethylamine, and/or molecular sieves. A nonlimiting representation of reaction 15 is provided in pathway (VIII) below.

5-tert-butyl-3-methyl-1,2-phenylene dibenzoate (BMPD) is shown as structure (IX) above. BMC, structure (I) above, is prepared by any of the foregoing processes/pathways. In other words, the process of producing BMPD may also include any of the foregoing processes for producing BMC.

In an embodiment, the reaction includes adding benzoyl chloride to a mixture of BMC, pyridine, and dichloromethane. Pyridine absorbs HCl, a by-product of the reaction.

In an embodiment, the process includes forming the BMPD by adding the benzoyl chloride to a reaction mixture composed of the BMC, acetonitrile and triethylamine. Triethylamine absorbs HCl, a by-product of the reaction. Use of acetonitrile and triethylamine advantageously provides an environmentally safe, and low health risk (non-toxic) process for BMPD production, and large-scale (i.e., greater than 10 g, or greater than 1 kg) production of BMPD in particular.

Figure 1:
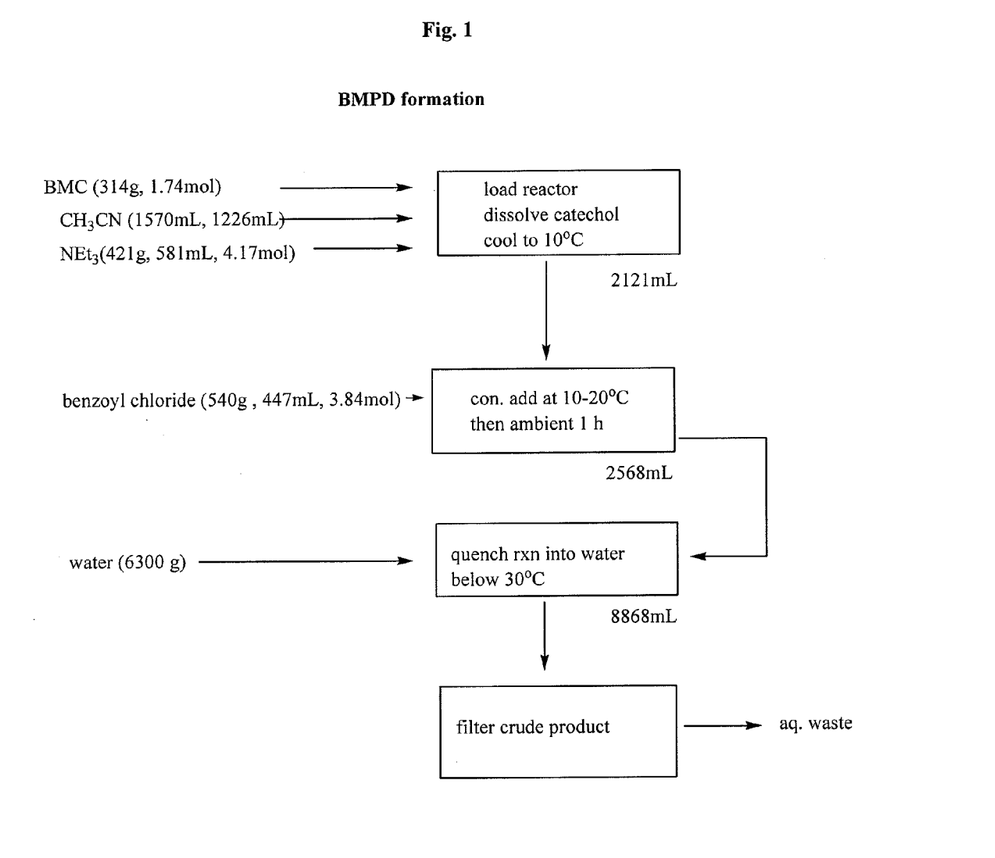
FIG. 1 is a flowchart showing a process for producing a substituted phenylene aromatic diester in accordance with an embodiment of the present disclosure.

In an embodiment, the process includes adding water to the reaction mixture (containing BMPD, acetonitrile triethylamine, benzoyl chloride, and BMC); and precipitating the BMPD. The solvent, acetonitrile, is soluble in water. Bounded by no particular theory, addition of the water quenches the reaction and changes the solubility of the solvent to precipitate the BMPD from solution (the "BMPD-precipitate"). Provision of the acetonitrile solvent system advantageously provides a simple, cost-effective and effective procedure for BMPD production, suitable for commercial or industrial scale. FIG. 1 shows a nonlimiting flowchart for BMPD production.

In an embodiment, the process includes purifying the BMPD, and forming a BMPD composition comprising greater than 98 wt %, or greater than 99 wt % BMPD. The purification of the BMPD includes performing one or more procedures on the BMPD-precipitate: recrystallization, extraction, concentration, washing, distillation, and any combination of the foregoing.

In an embodiment, the purification includes dissolving the BMPD-precipitate in a non-aqueous solvent (such as ethyl acetate), and extracting with water. Limited to no particular theory, it is believed water extraction removes ionic impurities and/or ionic byproducts from the non-aqueous phase thereby purifying the BMPD. The non-aqueous phase is dried (over $MgSO_4$) and concentrated by way of roto-evaporation (the "concentrate") in conjunction with a hydrocarbon wash (heptane) to remove organic by-products/impurities. Recrystallization yields a purified BMPD composition composed of greater than 98 wt %, or greater than 99 wt %, BMPD.

Figure 2:
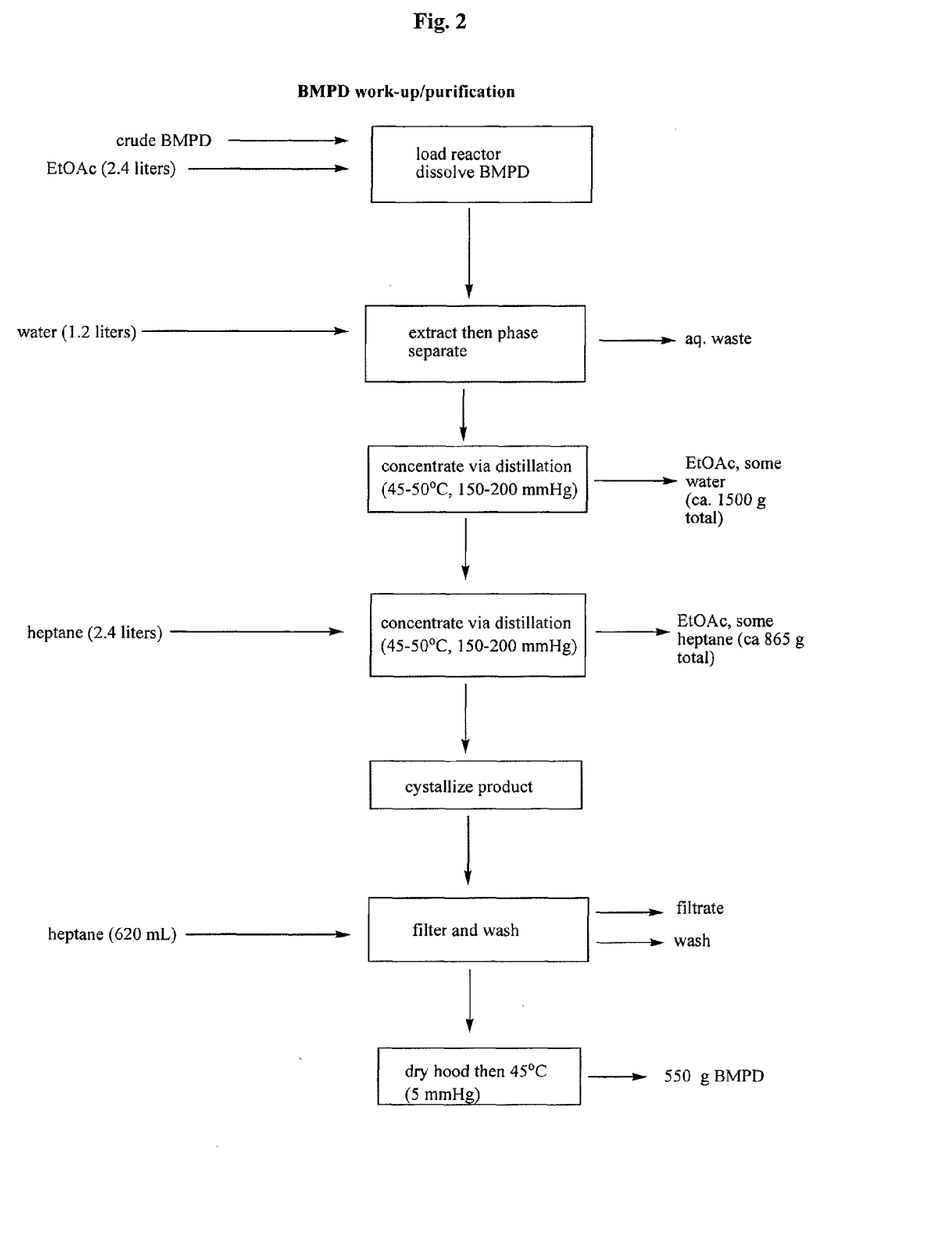
FIG. 2 is a flowchart showing a process for producing a substituted phenylene aromatic diester in accordance with an embodiment of the present disclosure.

In an embodiment, the purification includes distilling the concentrate in conjunction with a hydrocarbon wash (heptane). Filtration and drying yields a purified BMPD composition composed of greater than 98 wt %, or greater than 99 wt % BMPD. FIG. 2 shows a nonlimiting flowchart for the purification of the BMPD-precipitate.

The BMPD is advantageously applied as an internal electron donor in procatalyst/catalyst compositions for the production of olefin-based polymers (propylene-based polymers in particular) as disclosed in U.S. provisional application No. 61/141,902 filed on Dec. 31, 2008 and U.S. provisional application No. 61/141,959 filed on Dec. 31, 2008, the entire content of each application incorporated by reference herein.

Definitions

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

The term "substituted phenylene aromatic diester" includes substituted 1,2-phenylene aromatic diester, substituted 1,3-phenylene aromatic diester, and substituted 1,4-phenylene aromatic diester. In an embodiment, the substituted phenylene diester is a 1,2-phenylene aromatic diester with the structure (A) below:

(A)

wherein $R_1$-$R_{14}$ are the same or different. Each of $R_1$-$R_{14}$ is selected from a hydrogen, substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. At least one of $R_1$-$R_{14}$ is not hydrogen Test Methods $^1$H nuclear magnetic resonance (NMR) data is obtained via a Brüker 400 MHz spectrometer in $CDCl_3$ (in ppm).

By way of example, and not limitation, examples of the present disclosure are provided.

EXAMPLES

Example 1

Conversion of 3-methylcatechol to
5-tert-butyl-3-methylcatechol (Reaction 1)

A 1000 mL three neck flask equipped with stirrer, condenser and thermometer is charged with 3-methylcatechol (25.0 g, 0.20 mole), tert-butanol (38.0 mL, 0.40 mole) and 500 mL of heptane; followed by addition of sulfuric acid (98%, 20 g) slowly. The mixture is heated to 80° C. for 6 hrs until gas chromatography (GC) indicates the completion of the reaction. The solvent is removed in vacuo, and the residue is dissolved in $CH_2Cl_2$ and washed with water, $NaHCO_3$ (aq.), brine and dried ($Na_2SO_4$). Filtration and concentration yield 5-tert-butyl-3-methylcatechol (36 g, 84%). $^1$H NMR: 6.79 (s, 1H), 6.75 (s, 1H), 5.01 (br, 1H), 2.29 (s, 3H), 1.29 (s, 9H).

Example 2

Conversion of 2-hydroxy-3-methylbenzaldehyde to
3-methylcatechol (Reaction 2)

A 100-mL 3-neck round bottom flask, equipped with stirrer, reflux condenser, thermometer, dropping funnel is charged with 6.8 g of 2-hydroxy-3-methylaldehyde and 25 mL of 2N NaOH aqueous solution. With stirring, a diluted $H_2O_2$ is added in portion of 10 mL to maintain internal temperature between 40° C. to 50° C. After addition of the first portion of hydrogen peroxide, the temperature rises to 45° C. and a dark solution results. The temperature is allowed to fall to 40° C. before a second portion of hydrogen peroxide is added. After all the peroxide is added, the reaction mixture is allowed to cool to room temperature and is saturated with sodium chloride, and extracted with ether (3×50 mL). The combined extracts are dried over sodium sulfate, the ether is removed, and distilled to give product. $^1$H NMR: 6.73 (m, 3H), 2.89 (s, 3H).

Example 3

Conversion of o-cresol to
2-hydroxy-3-methylbenzaldehyde (Reaction 3)

A 1-L 4-neck round bottom flask, equipped with stirrer, reflux condenser, thermometer, nitrogen inlet and bubbler is charged with 20.64 mL of o-cresol and 14.0 g of paraformaldehyde. THF is charged via syringe followed by addition of triethylamine via dropping funnel. After stirring for another 10 min, o-cresol is added slowly via syringe, resulting in an opaque, light pink mixture that is refluxed for 4 hours. The reaction is cooled and diluted with 200 mL of ether, washed with 1 N HCl, water, and dried over $Na_2SO_4$. After removal of solvent under vacuum, the residue is purified by distillation to give 15.6 grams (57%) of product. $^1$H NMR: 11.3 (s, 1H), 9.89 (s, 1H), 7.41 (d, J=7.44 Hz, 2H), 6.95 (t, J=7.5 Hz, 1H), 2.30 (s, 3H).

Example 4

Conversion of 5-tert-butyl-3-methylcatechol to
5-tert-butyl-3-methyl-1,2-phenylene dibenzoate (Reaction 15)

A 250-ml round bottom flask is charged with 5-tert-butyl-3-methylcatechol (BMC) (0.025 mol), pyridine (0.05 mol, 1.0 equiv.), and dichloromethane (50 ml). The flask is cooled in an ice-water bath, and benzoyl chloride (0.1 mol, 1.0 equiv.) is added dropwise. Upon completion of addition, the reaction mixture is warmed to room temperature and stirred overnight. The mixture is diluted with additional dichloromethane, and washed with saturated $NH_4Cl$/1N HCl, water, saturated sodium bicarbonate, and brine consequently. The organic layer is collected and dried over magnesium sulfate. After filtration, the filtrate is concentrated, and the residue is dried in vacuo. Most of the crude products are pure enough, which can also be further purified by recrystallization from ethanol (for solid) or by distillation in vacuo to yield the product as white to yellow solid/liquid. Crude yield 98%. $^1$H NMR (500 MHz, $CDCl_3$, ppm): 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H).

Example 5

Conversion of 5-tert-butyl-3-methylcatechol to 5-tert-butyl-3-methyl-1,2-phenylene dibenzoate (Reaction 15)

A 500 mL three-neck round bottom flask with thermowell is fitted with an addition funnel/$N_2$ inlet, mechanical stirrer and a stopper. After the system is purged with $N_2$ the vessel is loaded with the 5-tert-butyl-3-methylcatechol (20.0 g, 0.11 mol) and $CH_3CN$ (100 mL). The mixture is stirred at ambient temperature until all the solids are dissolved. To the vessel is added triethylamine (26.8 g, 0.27 mol) and the internal temperature of the reaction is taken to 10° C. using a dry ice/water bath. Benzoyl chloride (34.4 g, 0.24 mol) is added dropwise keeping the temperature at 10-20° C. The addition takes about 30 minutes. The ice bath is removed and the thick slurry is allowed to stir at ambient temperature for 1 hour.

A 1-liter three neck round bottom flask with thermowell is fitted with a $N_2$ inlet, mechanical stirrer and a stopper. To the flask is added water (400 mL). The slurry from above is added in eight portions over about 20 min. The resulting slurry is stirred at ambient temperature for 30 minutes and then the solid is collected via filtration.

The crude solid is dissolved in EtOAc (150 mL) and extracted with water (75 mL). The aqueous phase is discarded and the EtOAc phase is dried over $MgSO_4$. The $MgSO_4$ is removed by filtration providing 175 g of light brown solution. The solution is concentrated on a rotary evaporator (45-50° C. bath @150-200 mmHg) taking 96 g of solvent overhead. Heptane (150 mL) is added and concentration is continued taking an additional 55 g of solvent overhead. The flask is removed from the roto-vap and a stir bar is added. A few seed crystals are added and the mixture stirred at room temperature. Crystallization begins almost immediately. The slurry is stirred at room temperature for about 1 hour and then the product is collected via filtration. The cake is washed with heptane (40 mL) and then dried to a constant weight (5 mmHg/40° C.) providing the product as off white crystals (35 g, 81%).

Example 6

Conversion of 5-tert-butyl-3-methylcatechol to 5-tert-butyl-3-methyl-1,2-phenylene dibenzoate (Reaction 15)

A 5 L three-neck round bottom flask with thermowell is fitted with an addition funnel/$N_2$ inlet, mechanical stirrer and a stopper. After the system is purged with $N_2$ the pot is loaded with the starting 5-tert-butyl-3-methylcatechol (314.3 g, 1.75 mol) and $CH_3CN$ (1570 mL). The mixture is stirred at ambient temperature until all the solids are dissolved. To the pot is added triethylamine (423 g, 4.17 mol) and the internal temperature of the reaction is taken to 10° C. using a dry ice/water bath. Benzoyl chloride (543 g, 3.84 mol) is added dropwise keeping the temperature at 10-20° C. Initially only half of the benzoyl chloride is added into the additional funnel to prevent all of the material from being added at once. The entire addition takes about 2 hours. The ice bath is removed and the thick slurry is allowed to stir at ambient temperature overnight.

A 12-liter three neck round bottom flask equipped with a bottom drain, thermowell fitted with a $N_2$ inlet, mechanical stirrer and a stopper. To the flask is added water (6.3 L). The slurry from above is added in portions over about 15 minutes and the reactor is rinsed with water (100 mL) and $CH_3CN$ (50 mL). The resulting slurry is stirred at ambient temperature for 2 hours and then the solid is collected via filtration. The solid is then placed in a storage container to allow for the second batch to be completed. The two batches are worked up together.

A second batch is run in the same manner.

Work Up:

The crude solid from 2 batches of the reaction of Example 6 (total 1968 g, water wet) is dissolved in EtOAc (4.8 L), extracted with water (2400 mL) and allowed to stir at ambient temperature overnight. The aqueous phase is discarded and the light brown solution of EtOAc (5529 g) is divided in two portions to distill.

Distillation #1

The solution (2824.9 g) is concentrated by overhead short-path distillation (40-45° C. overhead temperature, 250-300 mmHg) taking 1718 g of solvent overhead. Heptane (2.4 L) is added and concentration is continued taking an additional 926 g of solvent overhead. The mixture is allowed to cool to room temperature and is stirred overnight. The product is collected via filtration and the cake is washed with heptane (620 mL) and then dried to a constant weight (5 mmHg/25° C.) providing the product as off white crystals (636.6 g).

Distillation #2

The solution (2692.4 g) is concentrated by overhead short-path distillation (40-45° C. overhead temperature, 250-300 mmHg) taking 1545 g of solvent overhead. Heptane (2.4 L) is added and concentration is continued taking an additional 864 g of solvent overhead. The mixture is allowed to cool to room temperature and is stirred overnight. The product is collected via filtration and the cake is washed with heptane (620 mL) and then dried to a constant weight (5 mmHg/25° C.) providing the product as off white crystals (606.8 g).

A total of 1243.4 g is produced at 92% yield with a melting point 110-112° C. The material has a purity greater than 99 wt %.

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A process comprising:
   reacting, under reaction conditions, 5-tert-butyl-3-methylcatechol (BMC) with triethylamine and a member selected from the group consisting of an aromatic carboxylic acid and an aromatic carboxylic acid derivative; and
   forming 5-tert-butyl-3-methyl-1,2-phenylene dibenzoate (BMPD).

2. The process of claim 1 comprising adding benzoyl chloride to a reaction mixture comprising the BMC, acetonitrile and triethylamine; and forming the BMPD.

3. The process of claim 1 comprising adding water to the reaction mixture; and precipitating the BMPD.

4. The process of claim 1 comprising dissolving the precipitated BMPD and extracting with water.

5. The process of claim 1 comprising forming a BMPD composition comprising greater than 98 wt % BMPD.

6. The process of claim 1 further comprising:
   alkylating, under reaction conditions, 3-methylcatechol with a member selected from the group consisting of tert-butanol and isobutylene; and
   forming 5-tert-butyl-3-methylcatechol.

7. The process of claim 6 further comprising oxidizing, under reaction conditions, 2-hydroxy-3-methylbenzaldehyde; and forming the 3-methylcatechol.

8. The process of claim 6 further comprising formylating, under reaction conditions, o-cresol with paraformaldehyde;

forming 2-hydroxy-3-methylbenzaldehyde;

oxidizing, under reaction conditions, the 2-hydroxy-3-methylbenzaldehyde; and forming the 3-methylcatechol.

9. The process of claim 6 further comprising oxidizing, under reaction conditions, o-cresol; and forming the 3-methylcatechol.

10. The process of claim 1 further comprising:

oxidizing, under reaction conditions, 5-tert-butyl-3-methyl-2-hydroxybenzaldehyde; and forming 5-tert-butyl-3-methylcatechol.

11. The process of claim 10 further comprising formylating, under reaction conditions, 4-tert-butyl-2-methylphenol with formaldehyde; and forming the 5-tert-butyl-3-methyl-2-hydroxybenzaldehyde.

12. The process of claim 10 further comprising alkylating, under reaction conditions, o-cresol with a member selected from the group consisting of isobutylene and t-butanol to form 4-tert-butyl-2-methylphenol; and formylating, under reaction conditions, the 4-tert-butyl-2-methylphenol with formaldehyde to form the 5-tert-butyl-3-methyl-2-hydroxybenzaldehyde.

13. The process of claim 1 further comprising:

oxidizing, under reaction conditions, 4-tert-butyl-2-methylphenol; and forming 5-tert-butyl-3-methylcatechol.

14. The process of claim 13 further comprising:

alkylating, under reaction conditions, o-cresol with a member selected from the group consisting of tert-butanol and isobutylene; and forming the 4-tert-butyl-2-methylphenol.

15. The process claim 1 further comprising:

hydrolyzing, under reaction conditions, 2-halo-4-tert-butyl-6-methylphenol; and forming 5-tert-butyl-3-methylcatechol.

16. The process of claim 15 further comprising chlorinating, under reaction conditions, 4-tert-butyl-2-methylphenol; and forming 2-chloro-4-tert-butyl-6-methylphenol.

17. The process of claim 15 further comprising brominating, under reaction conditions, 4-tert-butyl-2-methylphenol; and forming 2-bromo-4-tert-butyl-6-methylphenol.

18. The process of claim 15 further comprising alkylating, under reaction conditions, o-cresol with a member selected from the group consisting of isobutylene and t-butanol to form 4-tert-butyl-2-methylphenol; and chlorinating the 4-tert-butyl-2-methylphenol to form 2-chloro-4-tert-butyl-6-methylphenol.

19. The process of claim 15 further comprising alkylating, under reaction conditions, o-cresol with a member selected from the group consisting of isobutylene and t-butanol to form 4-tert-butyl-2-methylphenol; and brominating the 4-tert-butyl-2-methylphenol to form 2-bromo-4-tert-butyl-6-methylphenol.

* * * * *